(12) United States Patent
Wiesman

(10) Patent No.: US 11,207,509 B2
(45) Date of Patent: Dec. 28, 2021

(54) METHOD AND DEVICE FOR DELIVERY OF A SOLUTION INTO A BODY ORIFICE

(71) Applicant: Wiesman Holdings, LLC, York, PA (US)

(72) Inventor: Jon Wiesman, York, PA (US)

(73) Assignee: Wiesman Holdings, LLC, York, PA (US)

( * ) Notice: Subject to any disclaimer, the term of this patent is extended or adjusted under 35 U.S.C. 154(b) by 132 days.

(21) Appl. No.: 16/009,887

(22) Filed: Jun. 15, 2018

(65) Prior Publication Data

US 2018/0361130 A1 Dec. 20, 2018

Related U.S. Application Data

(60) Provisional application No. 62/520,156, filed on Jun. 15, 2017.

(51) Int. Cl.
| | |
|---|---|
| *A61M 31/00* | (2006.01) |
| *A61B 17/42* | (2006.01) |
| *A61M 3/02* | (2006.01) |
| *A61B 8/08* | (2006.01) |
| *A61N 5/10* | (2006.01) |

(52) U.S. Cl.
CPC .......... *A61M 31/005* (2013.01); *A61B 17/42* (2013.01); *A61M 3/0279* (2013.01); *A61M 31/00* (2013.01); *A61B 8/481* (2013.01); *A61M 2202/048* (2013.01); *A61M 2210/1089* (2013.01); *A61M 2210/1475* (2013.01); *A61N 5/1007* (2013.01)

(58) Field of Classification Search
CPC ...... A61B 17/42; A61B 8/481; A61M 3/0279; A61M 31/00; A61M 2202/048
USPC ......................................................... 604/257
See application file for complete search history.

(56) References Cited

U.S. PATENT DOCUMENTS

| | | | |
|---|---|---|---|
| 845,249 A | 2/1907 | Morris | |
| 4,309,995 A * | 1/1982 | Sacco | A61M 3/0279 604/259 |
| 4,551,148 A | 11/1985 | Riley, Jr. et al. | |

(Continued)

FOREIGN PATENT DOCUMENTS

| | | |
|---|---|---|
| WO | 0101899 A1 | 1/2001 |
| WO | 2004098389 A2 | 11/2004 |

(Continued)

OTHER PUBLICATIONS

Notification of Transmittal, and the International Search Report and the Written Opinion of the International Searching Authority, or the Declaration, PCT/US2018/037827, dated Oct. 1, 2018, 12 pages.

(Continued)

*Primary Examiner* — Phillip A Gray
(74) *Attorney, Agent, or Firm* — Barley Snyder

(57) ABSTRACT

A diffusing applicator is provided and generally includes a head unit, and extension shaft, and a dispensing device. The head unit includes a fluid receiving space and a plurality of dispensing passageways in communication the fluid receiving space. The extension shaft is securely connected to head unit. The dispensing device holds a fluid and is connected to the extension shaft. The dispensing device is in communication with the plurality of dispensing passageways.

23 Claims, 8 Drawing Sheets

(56) References Cited

U.S. PATENT DOCUMENTS

| | | | |
|---|---|---|---|
| 5,406,961 | A | 4/1995 | Artal |
| 5,891,086 | A | 4/1999 | Weston |
| 6,375,970 | B1 | 4/2002 | Bieniarz |
| 6,419,646 | B1 | 7/2002 | Baxter-Jones |
| 6,994,667 | B2 | 2/2006 | Singh |
| 7,884,093 | B2 | 2/2011 | Creasy et al. |
| 8,317,729 | B2 | 11/2012 | O'Brien et al. |
| 8,408,212 | B2 | 4/2013 | O'Brien et al. |
| 8,517,960 | B2 | 8/2013 | Bauer et al. |
| 8,568,292 | B2 | 10/2013 | Shalon et al. |
| 8,727,986 | B2 | 5/2014 | Hall et al. |
| 9,399,112 | B2 * | 7/2016 | Shevgoor ............ A61M 25/007 |
| 2002/0052404 | A1 | 5/2002 | Hunter et al. |
| 2003/0181897 | A1 | 9/2003 | Thomas et al. |
| 2004/0097957 | A1 | 5/2004 | Jaker et al. |
| 2004/0215181 | A1 | 10/2004 | Christopherson et al. |
| 2005/0095245 | A1 | 5/2005 | Riley et al. |
| 2007/0142792 | A1 | 6/2007 | Terrill |
| 2007/0172507 | A1 | 7/2007 | Zupkas et al. |
| 2007/0172508 | A1 | 7/2007 | Zupkas et al. |
| 2008/0188829 | A1 | 8/2008 | Creasy |
| 2009/0024108 | A1 * | 1/2009 | Lee-Sepsick ........... A61P 15/00 |
| | | | 604/515 |
| 2009/0076494 | A1 | 3/2009 | Azure |
| 2010/0003297 | A1 | 1/2010 | Tobias et al. |
| 2010/0021519 | A1 | 1/2010 | Shenoy |
| 2011/0060349 | A1 | 3/2011 | Cheng et al. |
| 2012/0238894 | A1 | 9/2012 | Principe et al. |
| 2013/0239974 | A1 | 9/2013 | O'Brien et al. |
| 2013/0338639 | A1 | 12/2013 | Karpen |
| 2014/0073879 | A1 | 3/2014 | Cantor et al. |
| 2014/0276916 | A1 * | 9/2014 | Ahluwalia ........ A61M 25/0068 |
| | | | 606/119 |

FOREIGN PATENT DOCUMENTS

| | | |
|---|---|---|
| WO | 2007007301 A2 | 1/2007 |
| WO | 2007061896 A1 | 5/2007 |
| WO | 2008101862 A1 | 8/2008 |
| WO | 2010099211 A2 | 9/2010 |
| WO | 2013138263 A1 | 9/2013 |

OTHER PUBLICATIONS

Society for Maternal Fetal Medicine publications committee, with assistance of Berghella V. Progesterone and preterm birth prevention: translating clinical trials data into clinical practice. Am J Obstet Gynecol 2012; 206: 376-86.

Committee on Practice Bulletins—Obstetrics. Prediction and prevention of preterm birth. Obstet Gynecol 2012;120:964-73.

Hassan SS, Romero R, Vidyadhari D, Fusey S, Baxter J, Khandelwal M, et al for the Pregnant Trial. Vaginal progesterone reduces the rate of preterm birth in women with a sonographically short cervix: a multicenter, randomized, double-blind, placebo-controlled trial. Ultrasound Obstet Gynecol 2011; 38: 18-31.

O'Brien JM, Houseman BA, Allen AA, Barton JR. Methylcellulose gel is a superior contrast agent for ultrasound examination of the cervix in obstetrics patients Ultrasound Obstet Gynecol 2003; 21:149-51.

Hamilton, BE, Martin JA, Osterman MJK, Curtin SC, Brady E. Division of Vital Statistics. Births: Preliminary Data for 2013. National Vital Statistics Reports, vol. 63, No. 2, May 29, 2014.

Behrman RE, Stith Butler A. Committee on understanding premature birth and assuring healthy outcomes: causes, consequences, and prevention. Washington, DC: National Academies Press, 2007.

Cahill AG, Odibo AO, Caughey AB, Stamilio D, Hassan S, Macones G, et al. Universal cervical length screening and treatment with vaginal progesterone to prevent preterm birth: a decision and economic analysis. Am J Obstet Gynecol;2010:202:548.e1-8.

Werner EF, Hans CS, Pettker CM, Buhimischi CS, Copel J, Funai EF, et al. Universal cervical-length screening to prevent preterm birth: a cost-effectiveness analysis. Ultrasound Obstet Gynecol 2011; 38:32-7.

O'Brien JM, DeFranco EA, Adair CD, Lewis DF, Hall DR, How H, et al for the Progesterone Vaginal Gel Study Group. Effect of progesterone on cervical shortening in women at risk for preterm birth: secondary analysis from a randomized, double-blind, placebo-controlled trial. Ultrasound Obstet Gynecol 2009; 34: 653-59.

DeFranco EA, O'Brien JM, Adair CD, Lewis DF, Hall DR, Fusey S, et al. Vaginal progesterone is associated with a decreased risk of early preterm birth and improved neonatal outcome in women with a short cervix. Ultrasound Obstet Gynecol 2007; 30:697-705.

Romero R, Nicolaides KH, Conde-Agudelo A, Tabor A, O'Brien JM, Cetingoz E, et al. Vaginal progesterone in women with an asymptomatic sonographic short cervix in the midtrimester decreases preterm delivery and neonatal morbidity: a systematic review and meta-analysis of individual patient data. Am J Obstet Gynecol 2012; 206: 124.e1-19.

Berghella V, Rafael TJ, Szychowski JM, Rust OA, Owen J. Cerclage for short cervix on ultrasonography in women with singleton gestations and previous preterm birth: a meta-analysis. Obstet Gynecol 2011; 117:663-71.

* cited by examiner

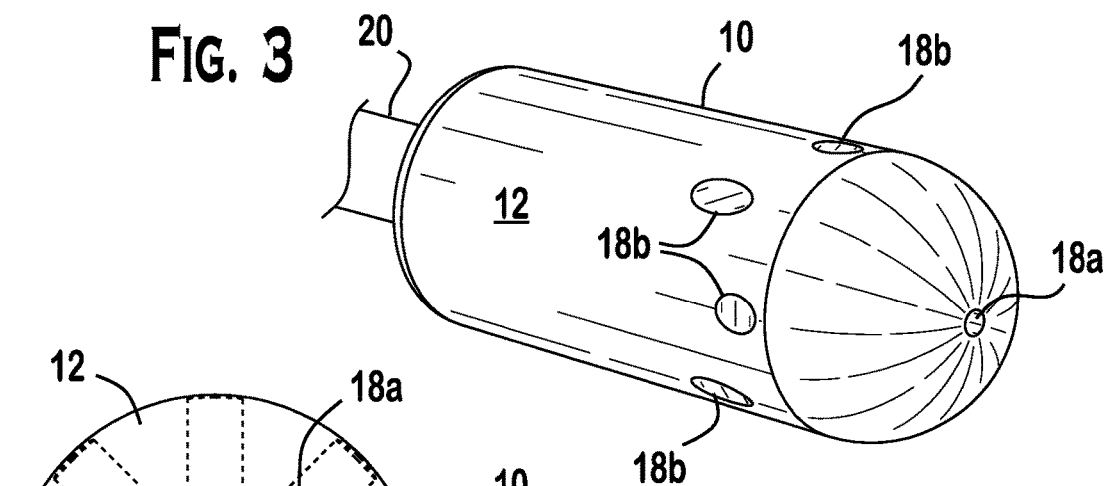
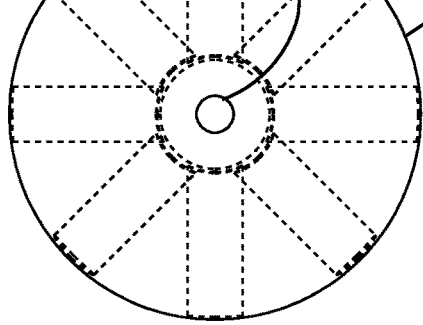
FIG. 4
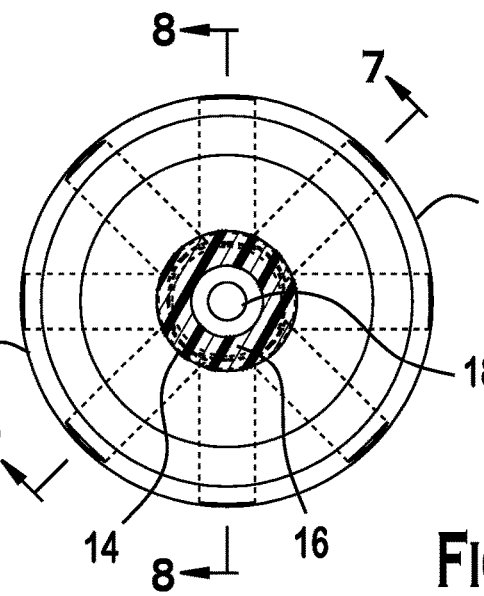
FIG. 5
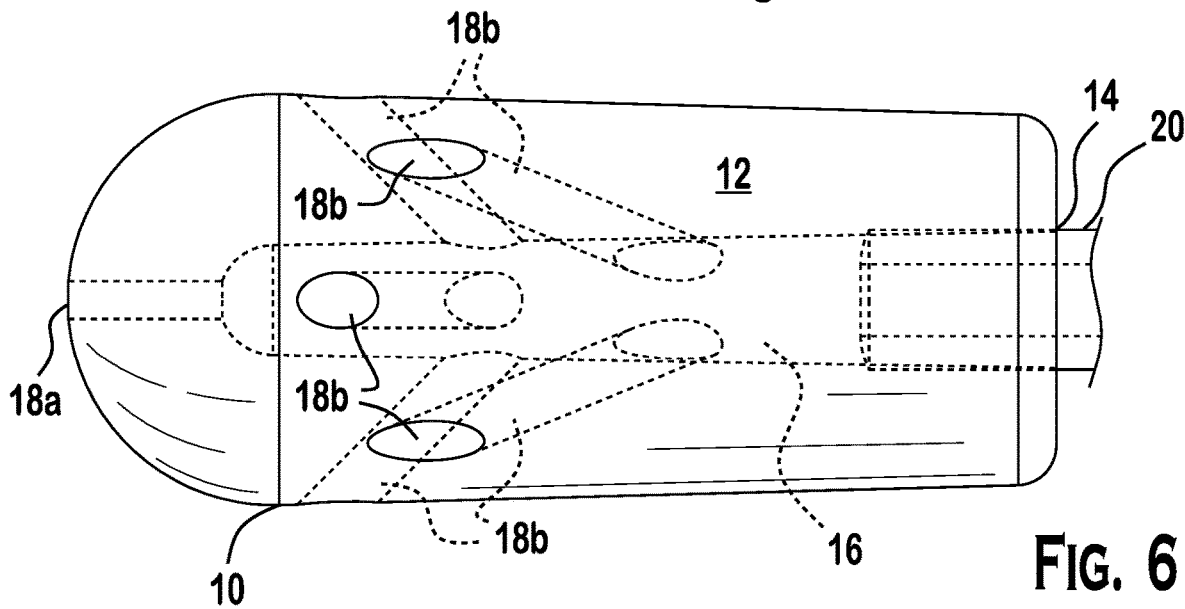
FIG. 6

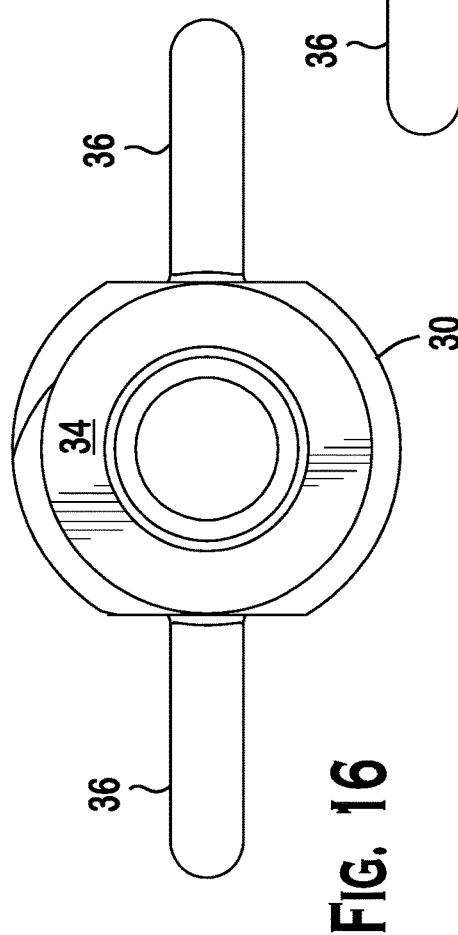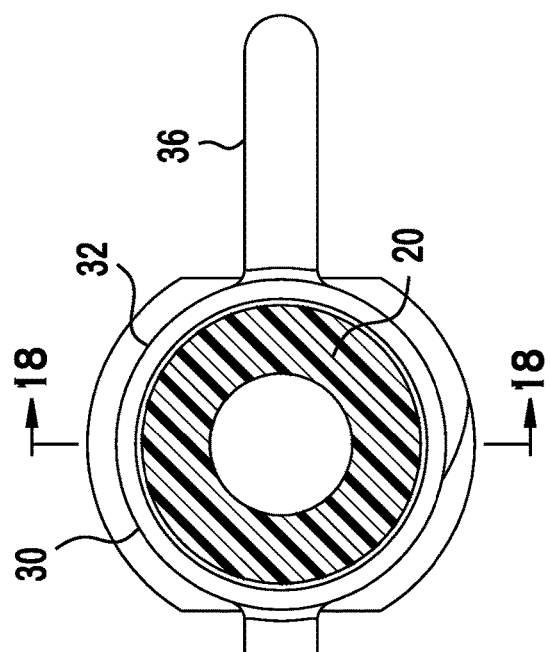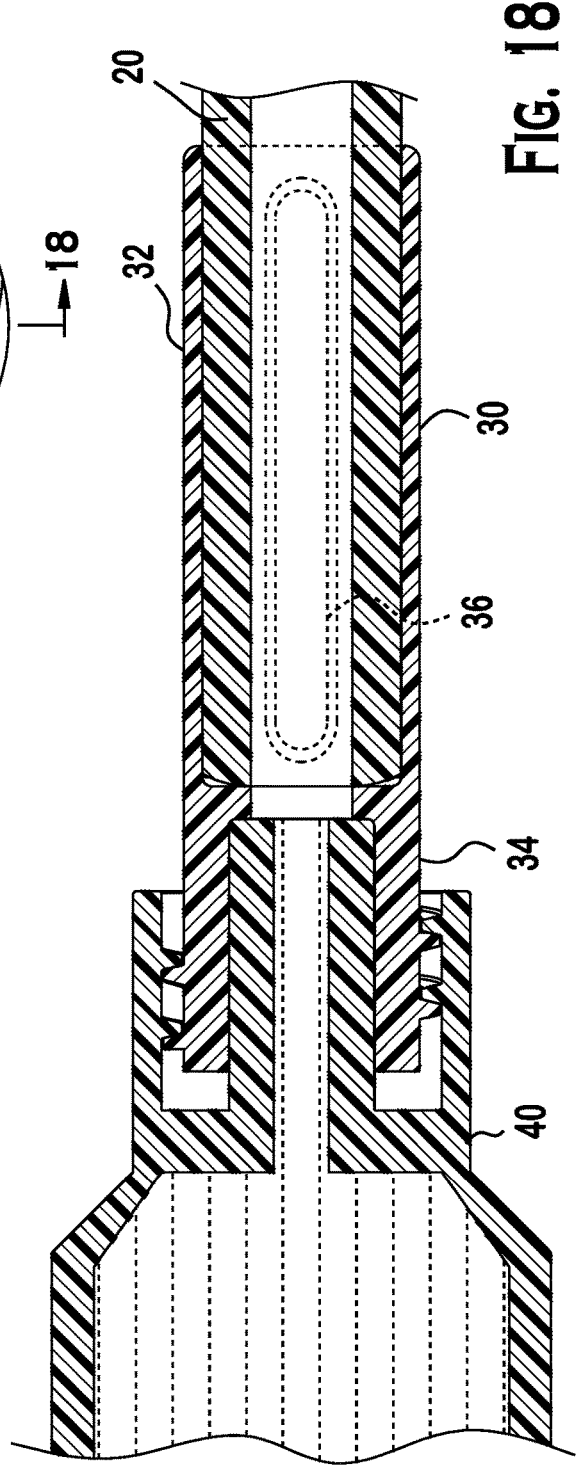

METHOD AND DEVICE FOR DELIVERY OF A SOLUTION INTO A BODY ORIFICE

CROSS-REFERENCE TO RELATED APPLICATIONS

This application claims the benefit of the filing of U.S. Provisional Application No. 62/520,156, filed Jun. 15, 2017.

FIELD OF THE INVENTION

The invention relates to a diffusing applicator 1 and, more particularly, a diffusing applicator for precisely delivering a viscous and/or non-viscous solution to a target area in the human body.

BACKGROUND

The incidence of preterm birth in the United States increased from 1990 until an all-time high was observed in 2006. Since that date, the rate of preterm birth has decreased 11.36% due to public health campaigns and a greater reliance on objective data to define the risk for preterm birth. Hamilton, B E, Martin J A, Osterman M J K, Curtin S C, Brady E., *Division of Vital Statistics, Births: Preliminary Data for 2013, National Vital Statistics Reports, Vol. 63, No. 2, May 29, 2014*.

Despite a reduction in incidence, the cost surrounding preterm birth remain staggering and the costs associated for one (1) baby in the neonatal intensive care unit (NICU) now can exceed $1,250,000.00. In 2006, the Institute of Medicine calculated the national expenditure exceeded 25 billion dollars annually to address the complication of preterm birth. Behrman R E, Stith Butler A., *Committee on understanding premature birth and assuring healthy outcomes: causes, consequences, and prevention*, Washington, D.C.: National Academies Press, 2007. Studies have now defined the most cost effective methods to reduce the frequency of preterm birth, including the measurement of cervical length rather than basing therapies upon obstetric history alone. Cahill A G, Odibo A O, Caughey A B, Stamilio D, Hassan S, Macones G, et al., *Universal cervical length screening and treatment with vaginal progesterone to prevent preterm birth: a decision and economic analysis*. Am J Obstet Gynecol; 2010:202:548.e1-8; also Werner E F, Hans C S, Pettker C M, Buhimischi C S, Copel J, Funai E F, et al., *Universal cervical-length screening to prevent preterm birth: a cost-effectiveness analysis*, Ultrasound Obstet Gynecol 2011; 38:32-7. One method is directed to a prophylactic strategy in women with a history of preterm birth, while another is directed to utilizing a therapeutic approach in those with premature cervical shortening. Of these two strategies, relying upon objective evidence to define an indication for treatment is likely superior as demonstrated in the largest randomized double-blind, placebo-controlled trial performed to date in singletons. O'Brien J M, DeFranco E A, Adair C D, Lewis D F, Hall D R, How H, et al., *Effect of progesterone on cervical shortening in women at risk for preterm birth: secondary analysis from a randomized, double-blind, placebo-controlled trial*, Ultrasound Obstet Gynecol 2009; 34: 653-59; also DeFranco E A, O'Brien J M, Adair C D, Lewis D F, Hall D R, Fusey S, et al., *Vaginal progesterone is associated with a decreased risk of early preterm birth and improved neonatal outcome in women with a short cervix*, Ultrasound Obstet Gynecol 2007; 30:697-705.

In addition, there is a desire to reduce unnecessary exposure to any intervention in in the population of pregnant women as an inherent.

Ultrasound provides an opportunity to define cervical integrity and performance by measurement of the cervical length. This measurement in conjunction with progesterone supplementation has shown to reduce the rate of preterm births. Romero R, Nicolaides K H, Conde-Agudelo A, Tabor A, O'Brien J M, Cetingoz E, et al., *Vaginal progesterone in women with an asymptomatic sonographic short cervix in the midtrimester decreases preterm delivery and neonatal morbidity: a systematic review and meta-analysis of individual patient data*, Am J Obstet Gynecol 2012, 206: 124e1-19. In fact, more data supports the use of this strategy based on objective measurement, a biomarker for preterm birth, than any other intervention in the history of obstetrics.

The measurement of cervical length is performed by ultrasound most commonly by either a transabdominal or transvaginal method. The transvaginal method requires an invasive, time-intensive procedure in addition to expertise. Therefore, the translation of research findings may not be as well adopted as needed if clinicians practicing in lower risk environments are not provided with the tools to allow optimal means to evaluate cervical contour and measure cervical length. Therefore, providing the opportunity to visualize the cervix is important to further reduce the rate of preterm birth.

Uniformity of any medical procedure is a desired goal as quality and safety and outcomes are improved. The application of a contrast into the vagina allows individuals with less expertise in cervical imaging to better define cervical landmarks improving the accuracy for measurement of cervical length.

This measurement is even more difficult when transabdominal imaging is exclusively performed. The use of a contrast in transabdominal, transperineal, or transvaginal imaging can improve assessment of anatomy, as contrast has been demonstrated to improve visualization with numerous other applications in radiology.

Therefore, there is a need for an improved method and device to deliver a solution contrast to improve the clarity of evaluating the cervix.

SUMMARY

An object of the invention, among others, is to provide a diffusing applicator 1 that improves the delivery of intravaginal contrast to evaluate a cervix Accordingly, a diffusing applicator is provided and generally includes a head unit, and extension shaft, and a dispensing device. The head unit includes a fluid receiving space and a plurality of dispensing passageways in communication the fluid receiving space. The extension shaft is securely connected to head unit. The dispensing device holds a fluid and is connected to the extension shaft. The dispensing device is in communication with the plurality of dispensing passageways.

BRIEF DESCRIPTION OF THE DRAWINGS

The present invention will be explained in greater detail with reference to embodiments and referring to the appended drawings, in which

FIG. 3 is a close-up perspective view a diffusing applicator 1 according to the invention, showing a head unit with a head unit with an extension shaft attached therewith;

FIG. 4 is a front view of the diffusing applicator 1 of FIG. 3;

FIG. 5 is a rear view of the diffusing applicator 1 of FIG. 3;

FIG. 6 is a side view of the diffusing applicator 1 of FIG. 3;

FIG. 16 is a front view of the adapter of FIG. 13;

FIG. 17 is a rear view of the adapter of FIG. 13;

FIG. 18 is a close-up sectional perspective view of an adapter according to the invention, shown connected to a known dispensing device

DETAILED DESCRIPTION OF THE EMBODIMENTS

Figure 1:
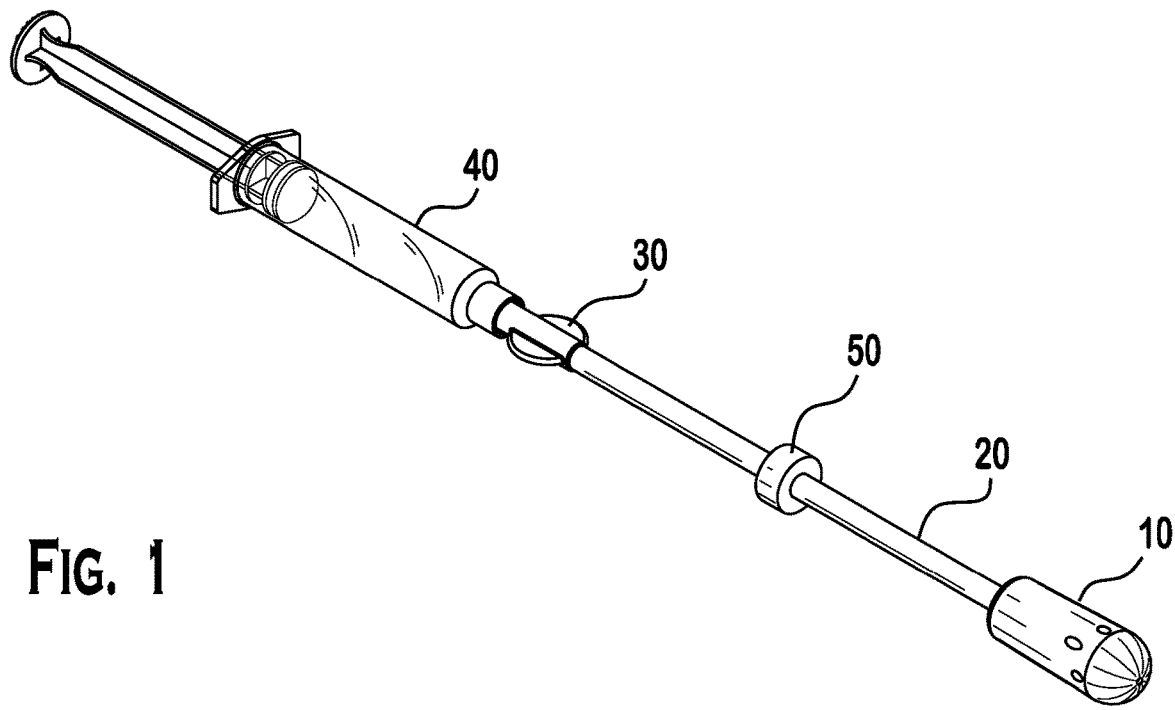
FIG. 1 is a perspective view of a diffusing applicator 1 according to the invention, shown connected with a known dispensing device.
Figure 2:
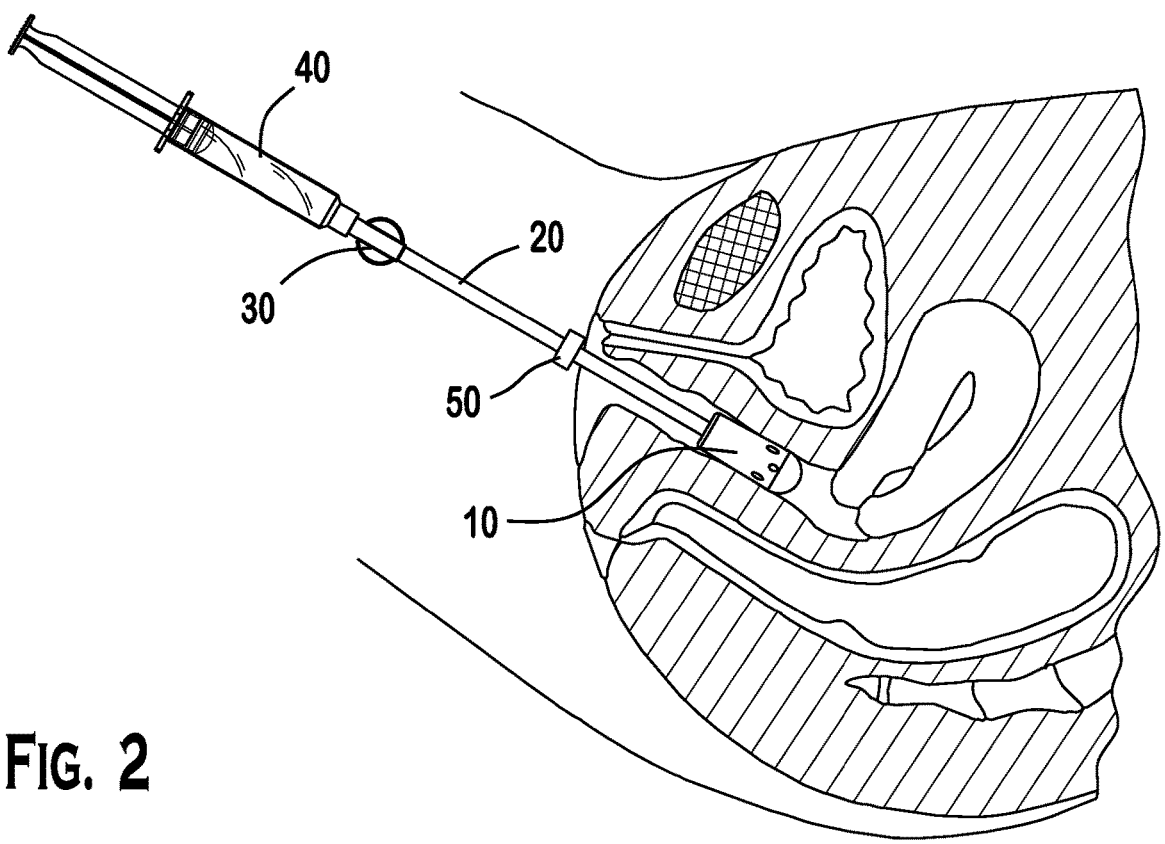
FIG. 2 is a side view of a diffusing applicator 1 according to the invention, showing an exemplary use therewith.

Now with reference to the figures, a diffusing applicator 1 according to the invention will be described and generally includes a head unit 10, an extension shaft 20, an adapter 30, and a dispensing device 40.

The diffusing applicator 1 according to the invention allows administration of a solution, such as a lubricant, anesthetic, pharmaceutical or contrast, into a body orifice, such as vagina uterus, urethra, rectum and/or nasal pharyngeal cavity.

As shown in FIGS. 1-9, the head unit 10 is a blunt shape member having a distal end and a proximal end. As shown, the head unit 10 is a is cylindrical shaped. However, one skilled in the art should appreciate that other shapes are possible and may be refined depending on the appropriate shape for the intended function of the diffusing applicator 1.

The head unit 10 can be designed in a multiple of shapes from a round structure to and oblong/oval structure, the primary goal of the head unit 10 is to safely enter into, deliver and/or place a solution, viscous and/or non-viscous medicated or non-medicated into a mammalian body orifice, namely the vagina and forward to and around the cervical os, but not limited to and/or into the uterus, urethra, rectum and/or nasal pharyngeal cavity by means of dispensing passageways 18 that can be positioned in any angular format around the structure.

The primary factor that ensures the safety of the diffusing applicator 1 is that the head unit 10 is rounded/smooth while being a larger diameter than the rigid and/or flexible structure, namely the extension shaft 20, that is incorporated into the structure namely the head unit 10.

The head unit 10 should also include a bulbous shape, such that the cervix or any membranes inadvertently encountered will at minimal risk for complications related to the application of a contrast agent which markedly differs from a syringe. Finally, the volume of contrast placed can be altered without the need for reinsertion of a device (syringe) which has edges and can be painful. None of these advancement occurred during or as a result of federally sponsored research.

The unique design of the head unit 10 may also be used for additional lubrication to reduce excessive perineal stretching aimed to reduce perineal lacerations and/or reducing trauma to the pelvic floor and/or levator muscles in regards to the expediting delivery of a child.

As shown, the head unit 10 generally includes outer walls 12, a shaft receiving opening 14, a fluid receiving space 16, and a plurality of dispensing passageways 18.

The outer walls 12 are generally made of plastic, such as rubber or resilient polymer, which are formed to include the shaft receiving opening 14 positioned at a distal end thereof, a fluid receiving space 16 positioned in a hollow center, and a plurality of dispensing passageways 18 extending from the fluid receiving space 16 toward a proximal end thereof.

The shaft receiving opening 14 is shaped and sized to correspond with the extension shaft 20 such that the outer walls 12 frictionally engage the extension shaft 20. The outer walls 12 are deformable and sized slightly smaller than the extension shaft 20 such that the extension shaft 20 is received through the shaft receiving opening 14 and secured by the outer walls along the distal end thereof. Therefore, when the extension shaft 20 is positioned through the shaft receiving opening 14, the extension shaft 20 is snug fit with the head unit 10 (see FIG. 7-9).

Figure 7:
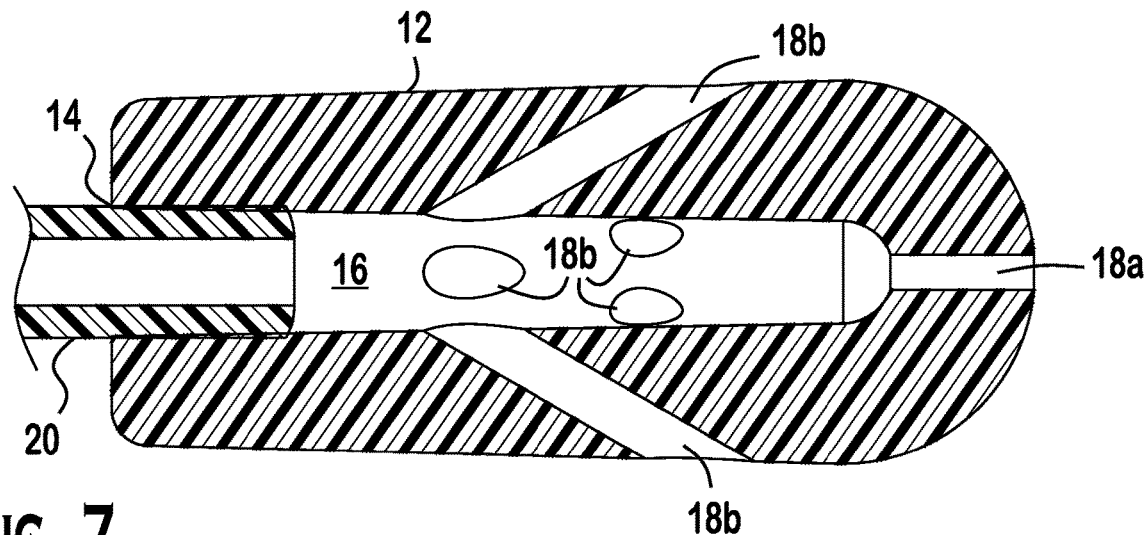
FIG. 7 is a sectional view of the diffusing applicator 1 of FIG. 5 taken along line 7-7.
Figure 8:
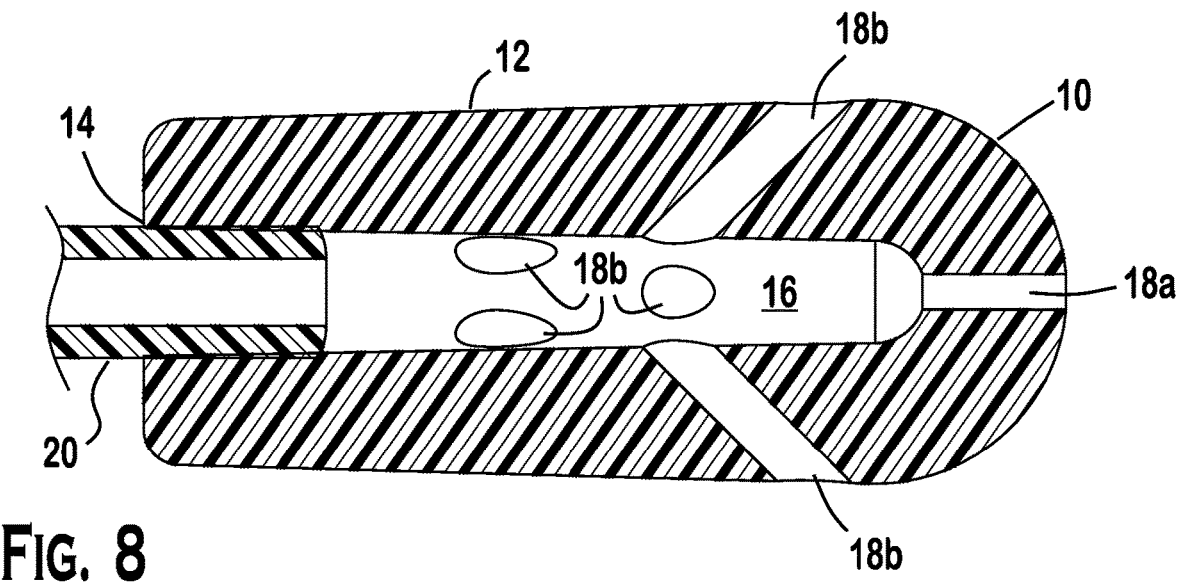
FIG. 8 is another sectional view of the diffusing applicator 1 of FIG. 5 taken along line 8-8.
Figure 9:
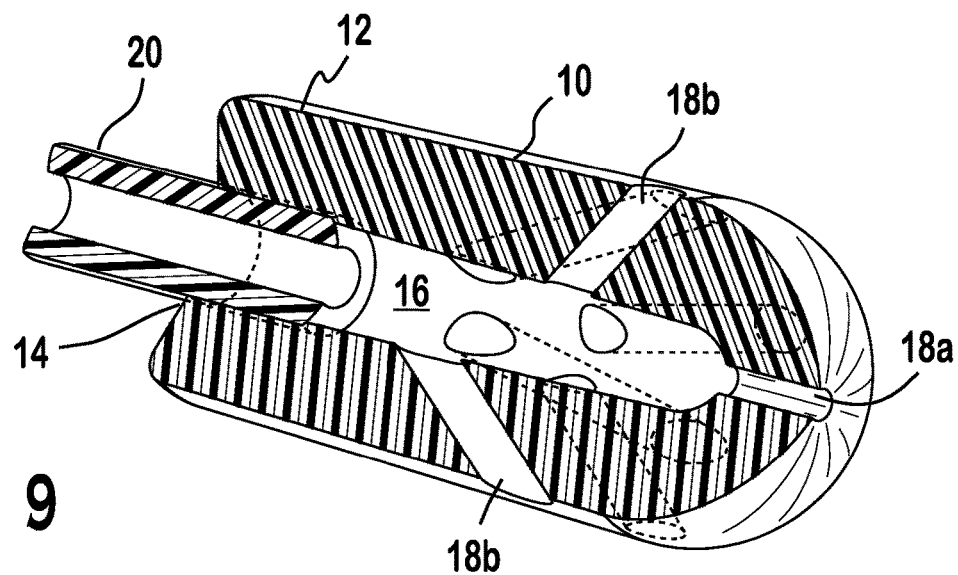
FIG. 9 is another sectional view of the diffusing applicator 1 of FIG. 5 taken along line 7-7.

In an exemplary embodiment as illustrated, each dispensing passageway 18 is a channel extending through the outer walls 12. As shown in FIGS. 7-9, each dispensing passageway 18 leads from the fluid receiving space 16 to on outer surface of the head unit 10.

As shown, the head unit 10 includes a primary dispensing passageway 18a and a plurality of secondary dispensing passageways 18b. In an exemplary, the primary dispensing passageway 18a extends laterally from the fluid receiving space 16 to on outer surface of the head unit 10. More particularly, the primary dispensing passageway 18a extends to a distal tip of the head unit 10. In contrast, the secondary dispensing passageways 18b extend from the fluid receiving space 16 to on outer surface of the head unit 10 at an angle. More particularly, the secondary dispensing passageway 18b extends to a sides of the head unit 10 and are spaced apart from the each other and positioned rearward of the primary dispensing passageway 18a. As a result, the head unit 10 according to the invention is provided with dispensing passageways 18 that produce an angular and lateral flow of a solution, viscous and/or non-viscous into a mammalian body orifice, for instance the vagina and forward on to the cervical os. However, one skilled in the art should appreciate that this design is not limited to this application, but and could be used in other applications, such as delivery of a the urethra, uterus, rectum and/or nasal pharyngeal cavity.

As shown in FIGS. 7-9, in an exemplary embodiment, the head unit includes three secondary dispensing passageways 18*b* extend at an approximate 45° degree angle and three secondary dispensing passageways 18*b* extend at an approximate 30° degree angle and are offset from each other and are positioned rearward of the secondary dispensing passageways 18*b*. As a result, the secondary dispensing passageways 18*b* evenly deliver solution about an outer surface of the outer walls 12. One skilled in the art should appreciate that the secondary dispensing passageways 18*b* could extend at various angles, including 90° degree with respect to the lateral placement of the primary dispensing passageway 18*a*.

The placement of the passageways 18 is in direct correlation to the safe placement of the solution, viscous and/or non-viscous into a mammalian body orifice, namely the vagina and forward to and around the cervical os, but not limited to and/or into the uterus, urethra, rectum and/or nasal pharyngeal cavity arrives via a syringe, but not limited to any structure, such as a bag/pouch or cartridge so that damage does not occur to the organ and/or orifice for which the device enters.

The head unit 10 design facilitates a specific and safe even disbursement of the viscous and/or non-viscous solution into a body cavity. In an alternative application, the head unit 10, as described, could be used with common therapy for prostate cancer by placing a lubricant void in the rectum ahead of radiation to reduce damage of surrounding tissue. In yet another application, the head unit 10 could be used for intavaginal brachytherapy.

Figure 10:
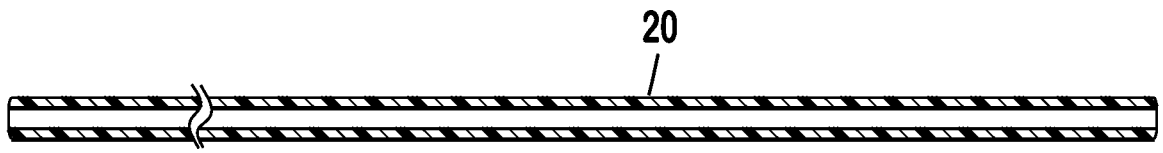
FIG. 10 is a sectional view of an extension shaft of a diffusing applicator 1 according to the invention.

Now with reference to FIG. 10, an extension shaft 20 for the diffusing applicator 1 and, more particularly, for a head unit 10 according to the invention, is shown. The extension shaft 20 is simply a known rigid and/or flexible structure "tube" to be inserted into the head unit 10 and an adapter 30 for a dispensing device 40, such as a syringe. The extension shaft 20 allows a viscous and/or non-viscous solution to flow without obstruction into the orifice and/or a cavity from the dispensing device through the head unit 10 by a length of the extension shaft 20.

Now with reference to FIGS. 13-18, an adapter 30 for the diffusing applicator 1 according to the invention is shown and connects with a dispensing device 40, such as a common luer lock syringe.

In an exemplary embodiment of the invention, the adapter 30 is a and/or attachment whereby the threads are present enabling a dispensing type container namely a "syringe" but not limited to any structure that can safely house a viscous and/or non-viscous solution to be locked on and/or slid in place onto and/or into the "receiver" assembly. Generally, the adapter 30 is made from a rigid plastic and generally includes a shaft receiving end 32 positioned at a proximal end, a dispensing unit receiving end 34 positioned at a distal end, and a handle section 36 positioned between the shaft receiving end 32 and the dispensing unit receiving end 34.

As shown, the adapter 30 is generally a tubular member having a fluid receiving channel 38 extending there through. The shaft receiving end 32 is a smooth tubular element such that a rigid and/or flexible extension shaft 20 can be inserted into fluid receiving channel 38 and the extension shaft 20 is frictionally secured to the adapter 30. In contrast, in an exemplary embodiment of the invention, the dispensing unit receiving end 34 is a tubular element having threads positioned on an outer surface thereof. As shown, this design would correspond with dispensing device 40 having matching threads along an inner surface thereof (see FIG. 18). However, one skilled in the art should appreciate that the dispensing unit receiving end 34 could include threads along an inner surface thereof, which would correspond with a dispensing device 40 having threads along an outer surface thereof.

In an exemplary embodiment, the adapter 30 may include a handle section 36. As shown, the handle section 36 include protuberances to facilitate clasping of the adapter 30. In the shown embodiment, the handle section 36 includes a pair of tabs 37 positioned on opposite sides thereof. As a result, the handle section 36 facilitates precise connection of the adapter 30 with the extension shaft 20 and the dispensing device 40. For instance, the handle section 36 allows the adapter to be precisely screwed onto a dispensing device 40 without compromising the integrity of either member.

Figure 19:
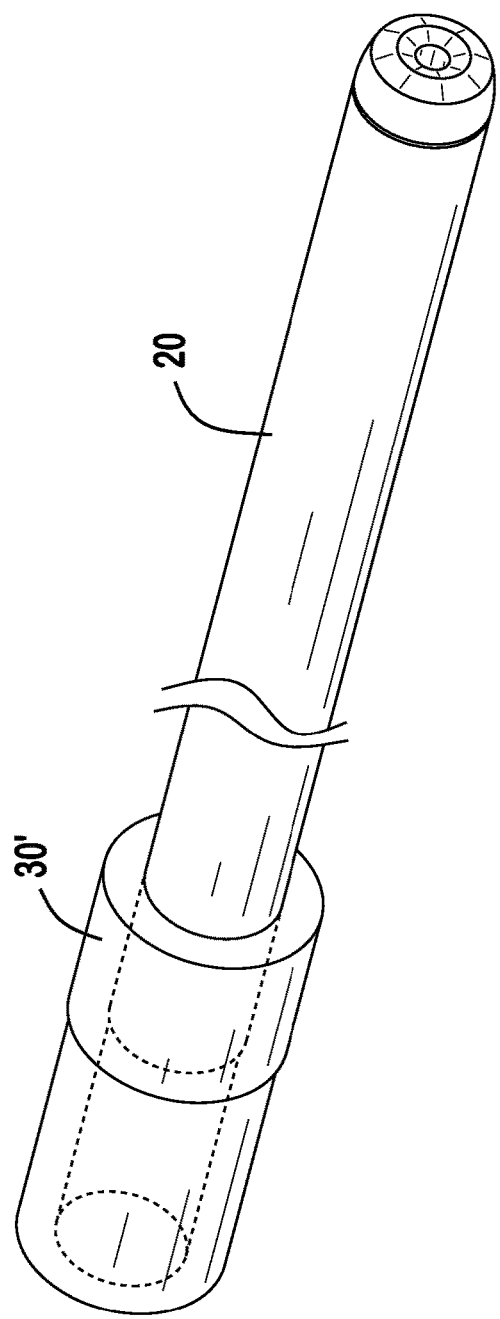
FIG. 19 is a perspective view of another diffusing applicator 1 according to the invention.
Figure 20:
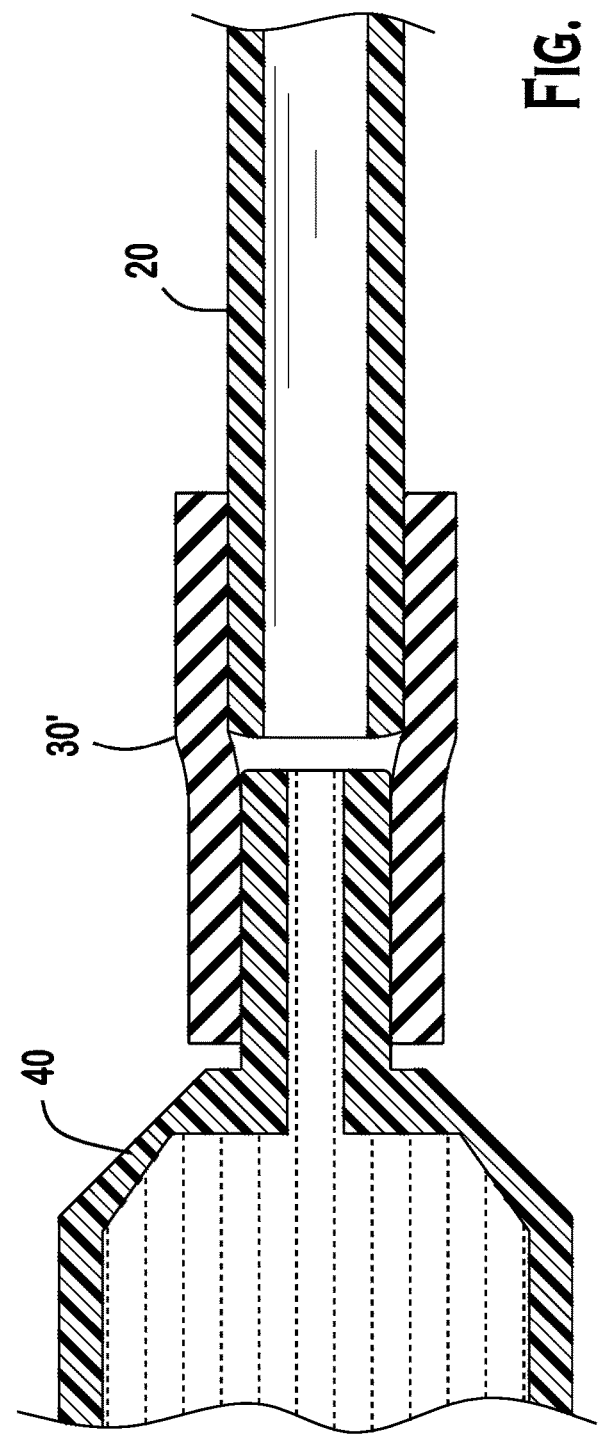
FIG. 20 is a close-up sectional view of the diffusing applicator 1 of FIG. 19, shown connected with a known dispensing device.

In alternative embodiment, as shown in FIGS. 19 and 20, the adapter 30' may be a simple sleeve that connects the extension shaft 20 and the dispensing device 40 through friction fit means. The adapter 30' may be a tubular member formed from a resilient plastic, such as rubber, and has in inner circumference slightly smaller than the extension shaft 20 and dispensing device 40. Upon assembly, the adapter 30' elastically deforms to first fit over the extension shaft 20 with inner walls of the adapter 30' bias the walls of the extension shaft 20 to secure the adapter 30' with the extension shaft 20. Likewise, the adapter 30' elastically deforms to then fit over the an end of the dispensing device 40 to secure the adapter 30' with the dispensing device 40.

As shown through the Figures, the dispensing device 40 is any known dispensing type container namely a "syringe", but not limited to any structure that can safely house a viscous and/or non-viscous solution to be locked on and/or slid in place onto and/or into the "receiver" assembly.

Figure 11:
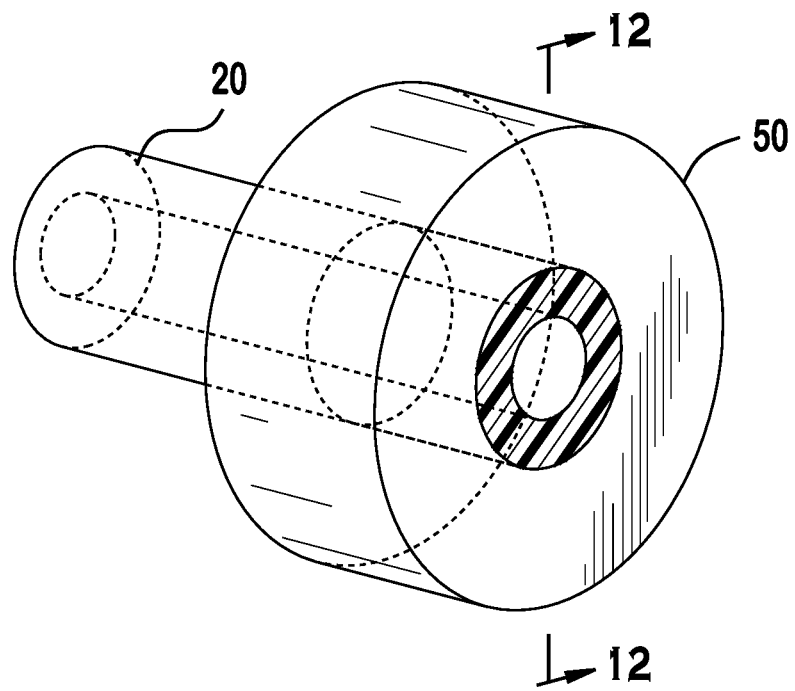
FIG. 11 is a close up view of a sliding stop and an extension shaft of a diffusing applicator 1 according to the invention.
Figure 12:
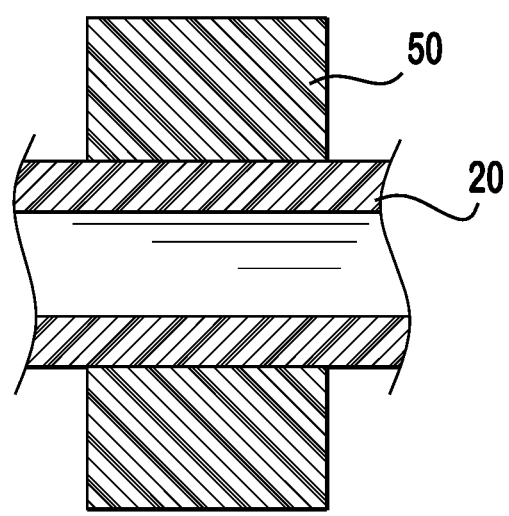
FIG. 12 is a sectional view of the sliding stop and extension shaft of FIG. 11
Figure 13:
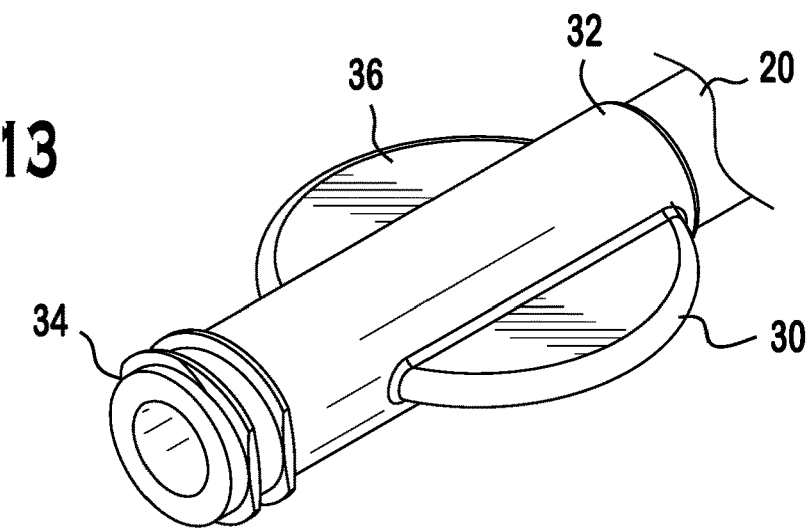
FIG. 13 is a perspective view of an adapter of a diffusing applicator 1 according to the invention.
Figure 14:
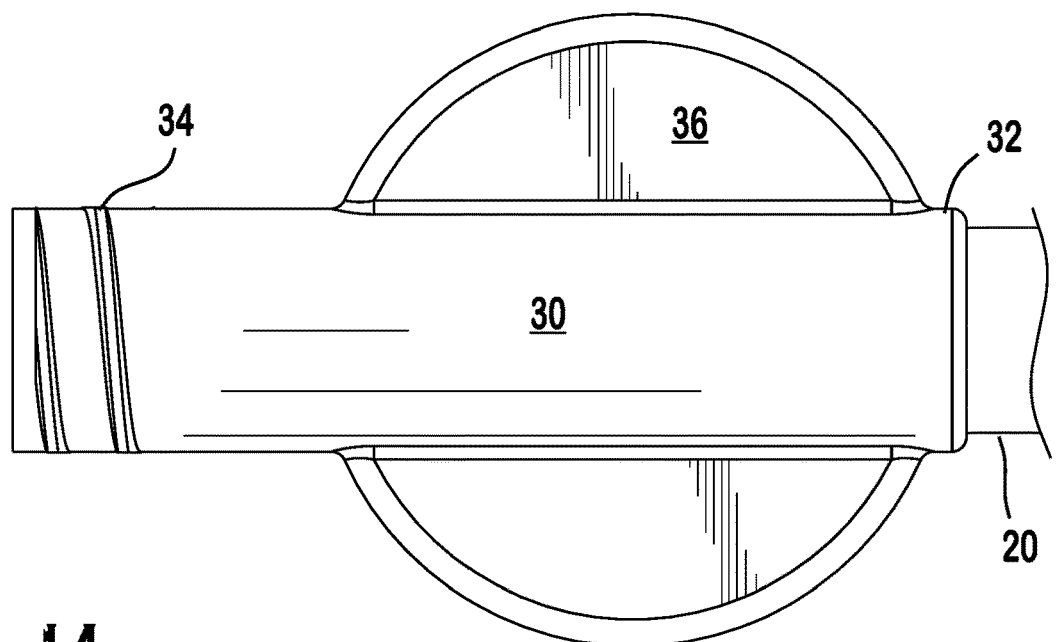
FIG. 14 is a top view of the adapter of FIG. 13.
Figure 15:
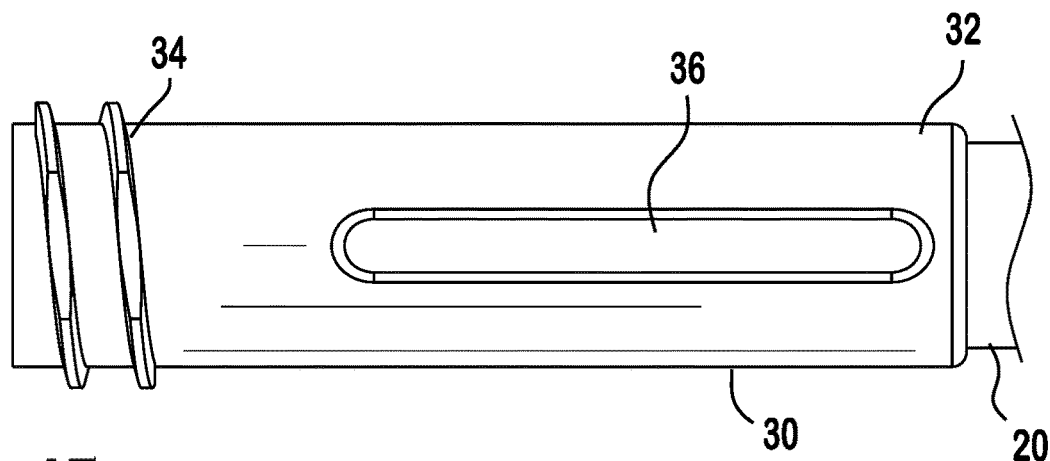
FIG. 15 is a side view of the adapter of FIG. 13.

Now, with reference to FIGS. 11 and 12, the diffusing applicator 1 according to the invention may further includes a slide 50 that is shaped and dimensions to forcibly slide up and down the extension shaft 20 to prevent the head unit 10 from advancing forward while allowing the practitioner to properly anesthetized area in urethra where the procedure will take place. The slide 50 has a primary function to prevent the advancement of the diffusing applicator 1 further than deemed necessary to properly perform the procedure by the practitioner (see FIG. 2). However, the slide 50 may also act as a premeasuring device that can be incorporated into the procedure especially if an ultrasound has predetermined the specific area where the procedure is to be conducted. The slide 50 can act as a safety stop for any procedure to be used as a depth marker by the practitioner to prevent any ancillary injury to the cervical os and/or mucosal tissue.

In an exemplary embodiment, the slide 50 is a ring shaped member having an inner circumference sized to receive, but bias, the outer walls of the extension shaft 20. As a result, the slide 50 can move up and down the extension shaft, but does so under force. Likewise, the slide 50 has an outer circumference that is larger than the head unit 10 such that when the head unit 10 is positioned in a body orifice, the slide 50 will not fit.

Now with reference to FIGS. 21-24, in a further embodiment, a diffusing applicator 1 according to the invention may be provided and directed to transurethral surgical procedures.

In the shown embodiments, the diffusing applicator 1 according to the invention may include alternative head unit 10 designs.

Figure 21:
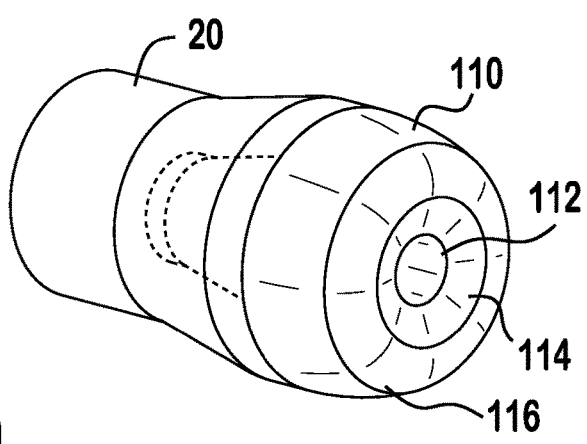
FIG. 21 is perspective view of another head unit of a diffusing applicator 1 according to the invention.
Figure 22:
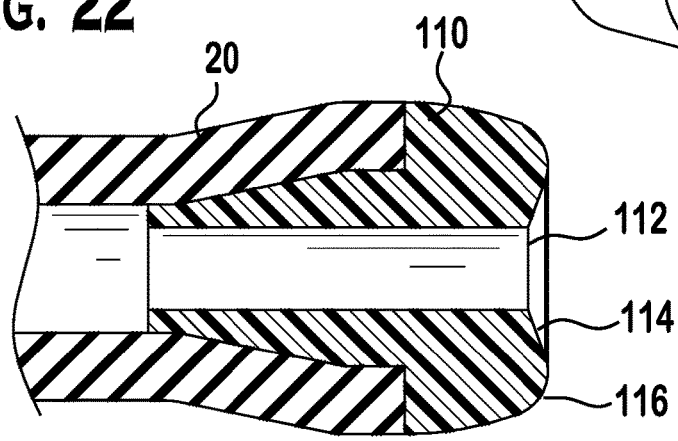
FIG. 22 is a sectional view of the head unit 10 unit of FIG. 21.

In an exemplary embodiment shown in FIGS. 21 and 22, another head unit 110 for a diffusing applicator 1 according to the invention is shown and generally includes a single center discharge tip for performing, for example, transurethral surgical procedures.

As shown in FIG. 22, the head unit 110 may include a single forward frontal discharge tip 112, which includes angled sides 114 at an end thereof that extend to a rounded polished tip 116 that would be flush with the extension shaft 20 and prevent any "snagging" of tissue when entering and/or exiting the urethra.

The diffusing applicator 1 according to the invention allows the application and/or deposit of a viscous/non-viscous medicated/non-medicated solution into the urethra providing an advanced anesthetized area.

Prior to the diffusing applicator 1 according to the invention, the medicated lubricant for transurethral surgical procedures was offered for sale in a 5 mL syringe with a slightly elongated tip. When administered, the medicated lubricant was only able to enter into the urethra a short way due to the naturally occurring vascular resistance in the urethra. As a result of this phenomenon, an entirely new design with the same concept was developed, most pertinently this device still diffuses/deliver a medicated viscous and/or non-viscous solution into the urethra for purposes of a low risk, non-invasive urological procedures.

Figure 23:
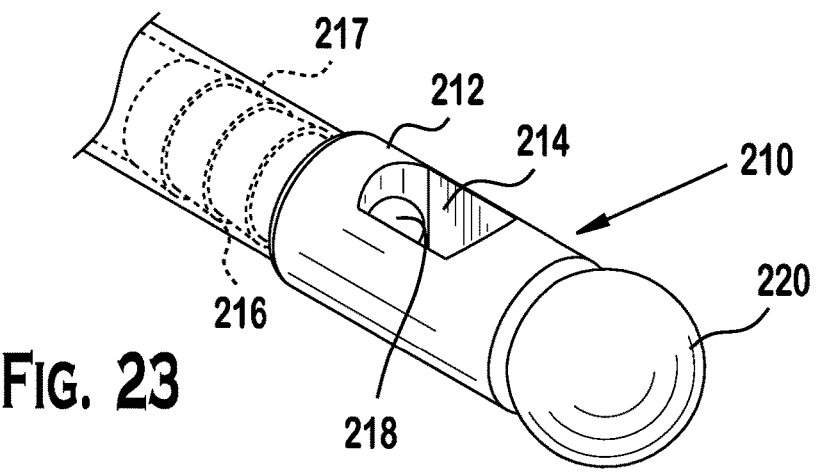
FIG. 23 is perspective view of another head unit and an extension shaft of a diffusing applicator 1 according to the invention.
Figure 24:
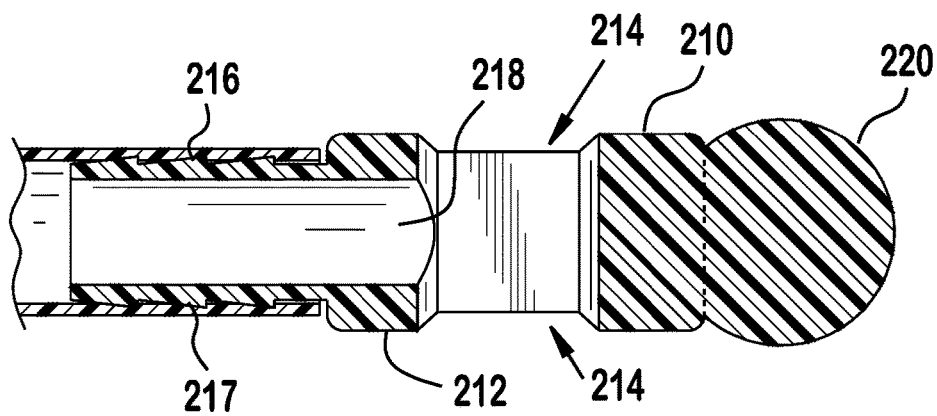
FIG. 24 is a sectional view of the head unit 10 unit and extension shaft of FIG. 23.

Now with reference to FIGS. 23 and 24, yet another head unit 210 for a diffusing applicator 1 according to the invention is shown and includes side discharge features for performing, for example, transurethral surgical procedures.

As shown, the head unit 210 generally includes a fluid discharge body 212 and insertion tip 220.

The fluid discharge body 212 generally includes a pair of side discharge passageways 214, an attachment section 216, and fluid receiving space 218.

The fluid discharge body 212 is a monolithic, generally cylindrical member with the fluid receiving space 218 extending through a center thereof. The side discharge passageways 214 are openings extending through the walls and positioned on opposite side s of the fluid discharge body 212. In the shown embodiment, the side discharge passageways 214 are generally box or rectangular shaped. However, one skilled in the art should appreciate that other designs are possible, including circular or oval shaped openings. As shown, in FIG. 24, the fluid receiving space 218 communicates with the side discharge opening 214.

The attachment section 216 is an elongated section of the fluid discharge body 212 and includes a plurality of hose barbs 217 positioned on an outside thereof. However, one skilled in the art should appreciate that other designs are possible. The circumference of the attachment section should be such that the fluid discharge body 212 would be substantially flush with the extension shaft 20 and prevent any "snagging" of tissue when entering and/or exiting the urethra.

The insertion tip 220 is a solid member and is secured to the fluid discharge body 212. The insertion tip 220 has a general spherical shape in the embodiment shown. The insertion tip 220 is free to sharp edges and rigid to allow easy and unobstructed entry into the body orifice.

The diffusing applicator 1 according to the invention allows the application and/or deposit of a viscous/non-viscous medicated/non-medicated solution into the urethra providing an advanced anesthetized area.

Prior to the diffusing applicator 1 according to the invention, the medicated lubricant for transurethral surgical procedures was offered for sale in a 5 mL syringe with a slightly elongated tip. When administered, the medicated lubricant was only able to enter into the urethra a short way due to the naturally occurring vascular resistance in the urethra. As a result of this phenomenon, an entirely new design with the same concept was developed, most pertinently this device still diffuses/deliver a medicated viscous and/or non-viscous solution into the urethra for purposes of a low risk, non-invasive urological procedures.

With reference to FIG. 1, assembly of a diffusing applicator 1 according to the invention will be described.

The slide 50 is positioned over the extension shaft 20 and the extension shaft 20 is securely connected to the head unit 10. The type of head unit 10, 110, 210 selected for the diffusing applicator 1 will depend on application, such as use for insertion into the vagina, uterus, urethra, rectum and/or nasal pharyngeal cavity. The extension shaft 20 is then connected to the dispensing device 40 with or without the adapter 30.

According to an embodiment of the invention, the diffusing applicator 1 according to the invention has a length that ranges anywhere from about 0.25" to about 24", with a diameter ranging from about 0.025" to about 0.50". The extension shaft 20 flexibility of the extension shaft 20 depends upon the solution chosen.

Now with reference to the Figure, uses of a diffusing applicator 1 will be described.

For instance, the diffusing applicator 1 according to the invention can provide contrast in the vagina to improve cervical imaging utilized a syringe to apply the contrast agent (saline or methylcellulose gel). The diffusing applicator 1 has addressed and resolved the short comings of all of the previous devices used to safely identify and measure the cervix.

For instance, the specific delivery and placement of a sterile medical lubricant around the cervical os, using the diffusing applicator 1, can reduce variation by allowing easier identification of the external cervical os. The diffusing applicator 1 allows for a volume of a viscous and/or non-viscous solution to be safely deployed around the cervical os. The volume of lubricant can be altered and provides the sonographer an opportunity to optimize the scan depending upon the method utilized.

The diffusing applicator 1 according to the invention is a device that functions totally different and relays upon a totally different methodology to arrive at a diagnosis of a shortened cervix, which in fact this protocol allows the diagnosis to be more uniform and this should be sufficient to differentiate between the two devices, when compared to that of the art.

The diffusing applicator 1 allows for a solution of varying viscosities namely a lubricant but not limited to any solution, viscous and/or non-viscous used to facilitate a procedure, medical and/or non-medical to facilitate a diagnosis so that a practitioner, namely an sonographer, but not limited to any medical technician, so that the volume of a solution, viscous and/or non-viscous will engage as a couplant that will provide a consistent resolution necessary to yield a uniform diagnosis.

The diffusing applicator 1 enables the solution viscous and/or non-viscous to be inserted and/or deposited into one of the above mentioned body orifices, of the volume of that solution, viscous and/or non-viscous. The solution acts as a void and/or couplant that in turn provides a medical practitioner a consistent resolution for Ultrasound, 2D Ultrasound, 3D Ultrasound, 4D Ultrasound, X-Ray, CAT Scan, C-Scope, MM and/or any other radiological imaging type device that requires a void and/or couplant necessary to achieve a uniform diagnosis.

The diffusing applicator 1 according to the invention allows for greater uniformity and accuracy for measurement of cervical length and easier identification of the shortened cervix. The diffusing applicator 1 according to the invention is designed to enhance translation for preterm prevention into lower risk, lower fidelity environments.

For instance, according to known practices, application of intravaginal contrast has been commonly performed via a syringe, but an improved methodology using the diffusing applicator 1 according to the invention can enhance translation of these important research findings. The diffusing applicator 1 rectifies previous short comings of known devices by delivering delivers a viscous and/or non-viscous solution to and around the cervical os.

In one exemplary aspect of the invention, the diffusing applicator 1 permits contrast to extrude laterally (at an angle away from the external os to minimize the potential for placement of gel into the endocervical canal or lower uterine segment) rather than through its most distal point like known devices.

Prior to the diffusing applicator 1 according to the invention, a medicated lubricant was offered for sale in a 5 mL syringe with a slightly elongated tip, when administered, the medicated lubricant was only able to enter into the urethra a short way due to the naturally occurring vascular resistance in the urethra. As a result of this phenomenon, an entirely new design with the same concept was developed, most pertinently this device still diffuses/deliver a medicated viscous and/or non-viscous solution into the urethra for purposes of a low risk, non-invasive urological procedures.

The diffusing applicator 1 according to the invention can appear in a numerous of designs depending upon the application and/or orifice for which the device is to safely deliver a viscous and/or non-viscous medicated and/or non-medicated solution to and around the cervical os and/or into the urethra, see below.

The diffusing applicator 1 according to the invention now allows for safer administration of a contrast to improve visualization of the cervix. The applicator according to the invention addresses and rectifies the short comings of the devices previously used to deliver and deliver a sterile viscous and/or non-viscous solution to and around the cervical os. The diffusing applicator 1 according to the invention is specifically designed such that contrast is extruded laterally (at an angle away from the external os to minimize the potential for placement of gel into the endocervical canal or lower uterine segment) rather than through its most distal point. This safety feature minimizes the risk for bacteria to be carried into the upper genital tract. The tip of the device is also designed as bulbous such that the cervix or any membranes inadvertently encountered will at minimal risk for complications related to the application of a contrast agent which markedly differs from a syringe. A smooth, rounded surface, specifically without rough edges means the potential for rupture of membranes due to inadvertent contact with fetal membranes is minimized.

The diffusing applicator 1 according to the invention is also designed for extrusion of contrast through multiple sites. This feature enhances the potential for contrast to spread throughout the desired location to improve visualization. In addition, multiple exit ports enhance safety.

Finally, the diffusing applicator 1 according to the invention also has features which enhance patient comfort. The use of a rounded tips of the head units 10, 110, 210 minimize patient pain and discomfort with application of a contrast. The volume of contrast placed can also now be altered without the need for reinsertion of a device such as a syringe and/or other rigid structure which can be painful. Therefore, the diffusing applicator 1 according to the invention is an improvement compared to past iterations used to place a solution, viscous and/or non-viscous into a mammalian body orifice, namely the vagina and forward to and around the cervical os, but not limited to and/or into the uterus, urethra, rectum and/or nasal pharyngeal cavity.

The foregoing illustrates some of the possibilities for practicing the invention. While certain embodiments of the invention have been described above, these descriptions are given for purposes of illustration and explanation. Variations, changes, modifications, and many other embodiments of the systems and methods disclosed may be adopted without departure from the scope and spirit of the invention. It is, therefore, intended that the foregoing description be regarded as illustrative rather than limiting, and that the scope of the invention is given by the appended claims together with their full range of equivalents.

What is claimed is:

1. A diffusing applicator comprising:
a head unit having a fluid receiving space and a plurality of dispensing passageways in communication with the fluid receiving space; the plurality of dispensing passageways including a primary extending from the end of the fluid receiving space to a distal tip thereof and a plurality of secondary dispensing passageways extending from sidewalls of the fluid receiving space to outer walls thereof and positioned such that the plurality of secondary dispensing passageways having openings staggered along a linear length of the sidewalls;
an extension shaft securely connected to the head unit;
a dispensing device for holding a fluid and connected to the extension shaft, the dispensing device in communication with the plurality of dispensing passageways such that the dispensing passageways are the exclusive outlets for the fluid from the applicator; and
a slide positioned over and moveable along the extension shaft and positionable along the extension shaft to prevent the head unit from advancing forward in an orifice and positioning the head unit adjacent a cervix such that the primary and secondary dispensing passageways evenly distribute fluid about the cervix.

2. The diffusing applicator according to claim 1, wherein the head unit is deformable and has a cylindrical bulbous shape.

3. The diffusing applicator according to claim 1, wherein the head unit is rounded and includes smooth surfaces.

4. The diffusing applicator according to claim 1, wherein the head unit has a larger diameter than the extension shaft.

5. The diffusing applicator according to claim 1, wherein the fluid receiving space extends through a center thereof and leads to a shaft receiving opening positioned on a distal end of the head unit.

6. The diffusing applicator according to claim 5, wherein the shaft receiving opening is shaped and sized to correspond with the extension shaft such that the head unit frictionally engage the extension shaft.

7. The diffusing applicator according to claim 1, wherein each of the plurality of dispensing passageways is a channel extending through outer walls of the head unit.

8. The diffusing applicator according to claim 7, wherein the plurality of dispensing passageways produce an angular and lateral flow of a fluid from the fluid receiving space.

9. The diffusing applicator according to claim 8, wherein the plurality of dispensing passageways include a primary dispensing passageway and a plurality of secondary dispensing passageways.

10. The diffusing applicator according to claim 9, wherein the primary dispensing passageway extends laterally from the fluid receiving space to on outer surface of the head unit.

11. The diffusing applicator according to claim 10, wherein the plurality of secondary dispensing passageways extend from the fluid receiving space to on outer surface of the head unit at an angle.

12. The diffusing applicator according to claim 11, the plurality of secondary dispensing passageways extend to sides of the head unit and are positioned apart from the each other and rearward of the primary dispensing passageway.

13. The diffusing applicator according to claim 1, further comprising an adapter 30 connecting the dispensing device to the extension shaft.

14. The diffusing applicator according to claim 13, wherein the adapter includes handle section positioned between a shaft receiving end and a dispensing unit receiving end.

15. The diffusing applicator according to claim 14, wherein the adapter is a tubular member having a fluid receiving channel extending there through.

16. The diffusing applicator according to claim 15, wherein the handle section includes a pair of tabs positioned on opposite sides thereof.

17. The diffusing applicator according to claim 1, wherein the slide is a ring shaped member having an inner circumference sized to receive and bias outer walls of the extension shaft.

18. A diffusing applicator comprising:
a head unit having a fluid receiving space and a dispensing passageway in communication with the fluid receiving space;
an extension shaft securely connected to the head unit;
a slide positioned over and moveable along the extension shaft and preventing procession of the head unit along a length to prevent the head unit from advancing forward in an orifice and positioning the head unit adjacent a cervix such that the dispensing passageway evenly distributes a fluid about the cervix; and
a dispensing device for holding the fluid and connected to the extension shaft, the dispensing device in communication with the dispensing passageway such that the dispensing passageway is the exclusive outlet for the fluid from the applicator.

19. The diffusing applicator according to claim 18, wherein the slide is a ring shaped member having an inner circumference sized to receive and bias outer walls of the extension shaft.

20. The diffusing applicator according to claim 18, wherein the dispensing passageway is a single forward frontal discharge tip having angled outer sidewalls at an end thereof.

21. The diffusing applicator according to claim 20, wherein the head unit includes a rounded polished tip that sits flush with the extension shaft.

22. The diffusing applicator according to claim 21, wherein the dispensing passageway is a side discharge passageway positioned on one side of the head unit.

23. The diffusing applicator according to claim 22, further comprising a second side discharge passageway positioned on another side of the head unit.

* * * * *